United States Patent
Eguchi (10) Patent No.: US 9,939,627 B2
(45) Date of Patent: Apr. 10, 2018

(54) OBJECTIVE OPTICAL SYSTEM FOR ENDOSCOPE

(71) Applicant: OLYMPUS CORPORATION, Hachioji-shi, Tokyo (JP)

(72) Inventor: Yosuke Eguchi, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/589,344

(22) Filed: May 8, 2017

(65) Prior Publication Data
US 2017/0242237 A1    Aug. 24, 2017

Related U.S. Application Data

(63) Continuation of application No. PCT/JP2016/066675, filed on Jun. 3, 2016.

(30) Foreign Application Priority Data

Jun. 23, 2015 (JP) ................................ 2015-125746

(51) Int. Cl.
*G02B 13/18* (2006.01)
*G02B 9/34* (2006.01)
(Continued)

(52) U.S. Cl.
CPC ........ *G02B 23/243* (2013.01); *A61B 1/00188* (2013.01); *G02B 13/04* (2013.01);
(Continued)

(58) Field of Classification Search
CPC ...... G02B 13/04; G02B 13/18; G02B 13/004; G02B 9/34; G02B 13/006; G02B 23/243;
(Continued)

(56) References Cited

U.S. PATENT DOCUMENTS

| 5,296,971 A * | 3/1994 | Mori ................... G02B 23/243 359/716 |
|---|---|---|
| 8,824,067 B2 | 9/2014 | Takato |
| 2013/0314805 A1 | 11/2013 | Takato |

FOREIGN PATENT DOCUMENTS

| JP | 04275514 A | 10/1992 |
|---|---|---|
| JP | 08286128 A | 11/1996 |

(Continued)

OTHER PUBLICATIONS

International Preliminary Report on Patentability (IPRP) dated Jan. 4, 2018 in counterpart International Application No. PCT/JP2016/066675.

*Primary Examiner* — Evelyn A Lester
(74) *Attorney, Agent, or Firm* — Holtz, Holtz & Volek PC (57) ABSTRACT

An objective optical system for endoscope includes, a first group having a positive refractive power, an aperture stop, and a second group having a positive refractive power, wherein the first group includes a first lens having a negative refractive power, and a second lens having a positive refractive power, the second group includes a cemented lens, and the cemented lens includes a third lens having a positive refractive power and a fourth lens having a negative refractive power, and the following conditional expressions (1), (2), (3), (4), (7) and (9) are satisfied:

$0.13 \leq La/Lb \leq 0.17$  (1), $-2.7 \leq f4/fs \leq -2.2$  (2),

$-0.7 \leq (ne2 \times f2)/(ne4 \times f4) \leq 0$  (3), $2.5 \leq vd3/vd4 \leq 3.5$  (4)

$-2.6 \leq r2o/rcc \leq -2$  (7), and $-1.2 \leq r2i/f2 \leq -0.9$  (9).

6 Claims, 5 Drawing Sheets

(51) Int. Cl.
  *G02B 23/24*    (2006.01)
  *A61B 1/00*     (2006.01)
  *G02B 13/04*    (2006.01)
  G02B 15/177     (2006.01)
  G02B 13/00      (2006.01)
  G02B 5/00       (2006.01)

(52) U.S. Cl.
  CPC ............. *A61B 1/00* (2013.01); *A61B 1/00096* (2013.01); *A61B 1/00163* (2013.01); *G02B 5/005* (2013.01); *G02B 9/34* (2013.01); *G02B 13/004* (2013.01); *G02B 13/006* (2013.01); *G02B 13/18* (2013.01); *G02B 15/177* (2013.01)

(58) Field of Classification Search
  CPC .. G02B 5/005; G02B 15/177; A61B 1/00096; A61B 1/00; A61B 1/00163
  USPC ........ 359/644, 645, 660, 661, 740, 753, 782
  See application file for complete search history.

(56) References Cited

FOREIGN PATENT DOCUMENTS

JP        5374667 B1   12/2013
WO     2013077139 A1    5/2013

\* cited by examiner

OBJECTIVE OPTICAL SYSTEM FOR ENDOSCOPE

CROSS-REFERENCE TO RELATED APPLICATION

The present application is a continuation application of PCT/JP2016/066675 filed on Jun. 3, 2016 which is based upon and claims the benefit of priority from Japanese Patent Application No. 2015-125746 filed on Jun. 23, 2015; the entire contents of which are incorporated herein by reference.

BACKGROUND OF THE INVENTION

Field of the Invention

The present invention relates to an objective optical system for endoscope.

Description of the Related Art

An endoscope is an optical apparatus that has been used in a medical field and an industrial field. Particularly, in the medical field, an endoscope is inserted into a body cavity and accordingly, an observation of inside of a body and acquiring of an image is carried out. Moreover, a diagnosis is made on the basis of images observed and images acquired. In such manner, an endoscope has been used for observation of an inside of a body and for diagnosis.

In an objective optical system for endoscope, an optical system of a retro-focus type has been adopted. In recent years, for improving an accuracy of diagnosis, a high quality of an image of endoscope has been sought. In objective optical systems for endoscope until now, improvement to a superior image quality such as by widening an angle of view, has been carried out while a lens arrangement of the retro-focus types maintained as it has been. Such objective optical system for endoscope has been disclosed in Japanese Patent Application Laid-open Publication No. Hei 4-275514 and Japanese Patent No. 5374667 Publication.

An objective optical system for endoscope disclosed in Japanese Patent Application Laid-open Publication No. Hei 4-275514 includes in order from an object side; a negative lens, a positive lens, and a cemented lens. The cemented lens includes a positive lens and a negative lens. In the objective optical system for endoscope of Japanese Patent Application Laid-open Publication No. Hei 4-275514, a curvature of field which was not corrected adequately previously, has been corrected favorably, and progress has been made in dealing with a large number of pixels of an image pickup element.

An objective optical system for endoscope disclosed in Japanese Patent No. 5374667 Publication includes in order from an object side; a negative lens, a positive lens, and a cemented lens. The cemented lens includes a positive lens and a negative lens. In the objective optical system for endoscope of Japanese Patent No. 5374667 Publication, an objective lens arrangement for endoscope of the retro-focus type has been adopted.

SUMMARY OF THE INVENTION

An objective optical system for endoscope of the present invention comprises in order from an object side, a first group having a positive refractive power, an aperture stop, and a second group having a positive refractive power, wherein the first group includes a first lens having a negative refractive power, of which an object side is a flat surface, and a second lens having a positive refractive power, and the second group includes a cemented lens, and the cemented lens includes a third lens having a positive refractive power and a fourth lens having a negative refractive power, and the following conditional expressions (1), (2), (3), (4), (7) and (9) are satisfied:

$$0.13 \leq La/Lb \leq 0.17 \quad (1),$$

$$-2.7 \leq f4/f \leq -2.2 \quad (2),$$

$$-0.7 \leq (ne2 \times f2)/(ne4 \times f4) \leq 0 \quad (3),$$

$$2.5 \leq vd3/vd4 \leq 3.5 \quad (4),$$

$$-2.6 \leq r2o/rcc \leq -2 \quad (7), \text{ and}$$

$$-1.2 \leq r2i/f2 \leq -0.9 \quad (9)$$

where,

La denotes a sum of air spaces along an optical axis of the objective optical system for endoscope, Lb denotes an overall length of the objective optical system for endoscope, f4 denotes a focal length of the fourth lens, f denotes a focal length of the objective optical system for endoscope, f2 denotes a focal length of the second lens, ne2 denotes a refractive index for an e-line of the second lens, ne4 denotes a refractive index for the e-line of the fourth lens, vd3 denotes Abbe number with reference to a d-line for the third lens, vd4 denotes Abbe number with reference to the d-line for the fourth lens, r2o denotes a radius of curvature of an object-side surface of the second lens, rcc denotes a radius of curvature of a cemented surface of the cemented lens, and r2i denotes a radius of curvature of an image-side surface of the second lens.

DETAILED DESCRIPTION OF THE INVENTION

Reasons for adopting such arrangements and effects thereof in an objective optical system for endoscope according to the present embodiment will be described below by referring to the accompanying diagrams. However, the present invention is not limited to the objective optical system for endoscope according to the embodiment described below.

An objective optical system for endoscope of an embodiment includes in order from an object side, a first group having a positive refractive power, an aperture stop, and a second group having a positive refractive power, wherein the first group includes a first lens having a negative refractive power, of which an object side is a flat surface, and a second lens having a positive refractive power, and the second group includes a cemented lens, and the cemented lens includes a third lens having a positive refractive power and a fourth lens having a negative refractive power, and the following conditional expressions (1), (2), (3), and (4) are satisfied:

$$0.13 \leq La/Lb \leq 0.17 \quad (1),$$

$$-2.7 \leq f4/f \leq -2.2 \quad (2),$$

$$-0.7 \leq (ne2 \times f2)/(ne4 \times f4) \leq 0 \quad (3), \text{ and}$$

$$2.5 \leq vd3/vd4 \leq 3.5 \quad (4)$$

where,

La denotes a sum of air spaces along an optical axis of the objective optical system for endoscope, Lb denotes an overall length of the objective optical system for endoscope, f4 denotes a focal length of the fourth lens, f denotes a focal length of the objective optical system for endoscope, f2 denotes a focal length of the second lens, ne2 denotes a refractive index for an e-line of the second lens, ne4 denotes a refractive index for the e-line of the fourth lens, vd3 denotes Abbe number with reference to a d-line for the third lens, and vd4 denotes Abbe number with reference to the d-line for the fourth lens.

Figure 1:
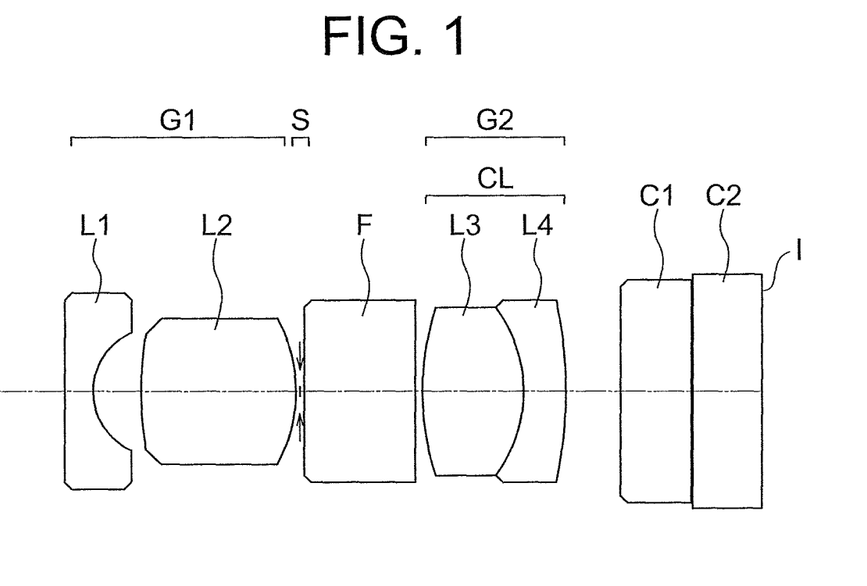
FIG. 1 is a diagram showing an objective optical system for endoscope according to an embodiment.

The objective optical system for endoscope of the present embodiment will be described below. FIG. 1 is a diagram showing the objective optical system for endoscope of the present embodiment.

To deal with small-sizing of an optical system, it is necessary to lessen the number of lenses in the optical system. On the other hand, as an objective optical system for endoscope, it is necessary to maintain a wide angle of view. Therefore, in the objective optical system for endoscope of the present embodiment, an optical system includes four lenses and the four lenses are arranged such that the lens arrangement is made to be a retro-focus type.

Specifically, the objective optical system for endoscope of the present embodiment includes in order from an object side, a first group G1 having a positive refractive power, an aperture stop S, and a second group G2 having a positive refractive power. An optical filter F is disposed between the first group G1 and the second group G2. A cover glass C1 and a cover glass C2 are disposed on an image side of the second group G2.

The optical filter F is a filter such as an infra-red absorbing filter. A coating that cuts laser light of a semiconductor laser may be applied to an image-side surface of the optical filter F. The cover glass C2 is a cover glass such as a cover glass of an image pickup element. The cover glass C1 and the cover glass C2 may have been cemented. I is an image plane (image pickup surface).

By the objective optical system for endoscope including the first group G1 having a positive refractive power, the aperture stop S, and the second group G2 having a positive refractive power, a balanced aberration correction becomes possible.

Moreover, the first group G1 includes a first lens L1 having a negative refractive power and a second lens L2 having a positive refractive power. The second group G2 includes a cemented lens CL. An object-side surface of the first lens L1 is a flat surface. The cemented lens CL includes a third lens L3 having a positive refractive power and a fourth lens L4 having a negative refractive power.

Here, the refractive power of the first lens L1 is a negative refractive power. Whereas, a combined refractive power of the second lens L2 and the cemented lens CL becomes a positive refractive power. In such manner, in the objective optical system for endoscope of the present embodiment, an optical system of retro-focus type is realized by four lenses. Consequently, in the objective optical system for endoscope of the present embodiment, both small-sizing of the optical system and securing of a wide angle of view are achieved.

Moreover, in the objective optical system for endoscope of the present embodiment, conditional expressions (1), (2), (3), and (4) are satisfied.

Conditional expression (1) is a conditional expression related to small-sizing of the optical system, and is a conditional expression related to the sum of air spaces (hereinafter, referred to as 'air length') along the optical axis in the objective optical system for endoscope. By satisfying conditional expression (1), it is possible to make the optical system small-sized.

In a case of falling below a lower limit value of conditional expression (1), since the air length becomes short, designing of a holding frame that holds a lens becomes difficult. Moreover, focus adjustment cannot be carried out. Thus, in a case of falling below the lower limit value of conditional expression (1), assembling of the optical system becomes difficult. In a case of exceeding an upper limit value of conditional expression (1), since the air length becomes long, the overall length of the optical system becomes long. Consequently, the small-sizing of the optical system cannot be carried out.

The air length is the sum of air spaces between a lens surface nearest to object up to an image plane. The overall length of the objective optical system for endoscope is a length obtained by adding the back focus to a distance from the lens surface nearest to object up to a lens surface nearest to image. The back focus is a length from the lens surface nearest to image up to the image plane, and is a length when not subjected to air conversion.

Here, it is preferable that the following conditional expression (1') be satisfied instead of conditional expression (1).

$$0.15 \leq La/Lb \leq 0.17 \tag{1'}$$

Conditional expression (2) is a conditional expression related to the small-sizing of the optical system, and is an expression in which a ratio of the focal length of the fourth lens and the focal length of the overall objective optical system for endoscope is taken. The focal lengths are focal lengths for the e-line. By satisfying conditional expression (2), it is possible to make the optical system small-sized.

In a case of falling below a lower limit value of conditional expression (2), since the focal length of the fourth lens becomes small, the negative refractive power of the fourth lens becomes small. Consequently, correction of a chromatic aberration becomes excessive. For correcting the chromatic aberration that has been corrected excessively, it is preferable to make short a focal length of the first lens. However, when the focal length of the first lens is made short to an extent such that the correction of the chromatic aberration is adequate, the negative refractive power in the overall optical system becomes large. In this case, since aberrations such as a spherical aberration and a coma are deteriorated, an imaging performance of the optical system is degraded.

In a case of exceeding an upper limit value of conditional expression (2), since the focal length of the fourth lens L4 becomes large, the negative refractive power of the fourth lens L4 becomes large. Consequently, correction of the chromatic aberration is inadequate. When an attempt is made to correct the chromatic aberration that has been corrected inadequately, the positive refractive power of the overall optical system becomes large. In this case, either the overall length of the optical system becomes long or a lens diameter becomes large. Consequently, small-sizing of the optical system becomes difficult.

In order to prevent the peripheral resolution from being degraded due to a manufacturing error, it is necessary to correct a curvature of field adequately. For this, it is necessary to make Petzval sum small. Petzval sum is obtained by summing a reciprocal of a product of a refractive index and a focal length of a lens, for all lenses.

Conditional expression (3) is an expression in which a ratio of a product of a refractive index and a focal length of the second lens and a product of a refractive index and a focal length of the fourth lens is taken. By satisfying conditional expression (3), it is possible to prevent the degradation of the peripheral resolution due to the manufacturing error.

In a case of falling below a lower limit value of conditional expression (3), Petzval sum cannot be made adequately small. In this case, since the curvature of field cannot be corrected favorably, it becomes difficult to prevent the degradation of peripheral resolution. In a case of exceeding an upper limit value of conditional expression (2), the chromatic aberration cannot be corrected adequately.

Here, it is preferable that the following conditional expression (3') be satisfied instead of conditional expression (3).

$$-0.7 \leq (ne2 \times f2)/(ne4 \times f4) \leq -0.3 \tag{3'}$$

Conditional expression (4) is a conditional expression related to the overall length of the optical system. By satisfying conditional expression (4), since it is possible to correct a chromatic aberration of magnification, it is possible to prevent the degradation of the peripheral resolution.

For correcting the chromatic aberration of magnification favorably, it is necessary to take into account Abbe number (dispersion) for each lens. However, in the objective optical system for endoscope, from a view point of biocompatibility, there are few optical glasses that can be selected for the first lens. The chromatic aberration of magnification can be corrected favorably by increasing lenses, but increasing the lenses is not favorable from a view point of small-sizing of the optical system. For such reason, for correcting favorably the chromatic aberration of magnification occurred in the first lens without making the overall length of the optical system long, it is necessary to set appropriately Abbe number for the cemented lens.

In a case of falling below a lower limit value of conditional expression (4), since Abbe number for the fourth lens becomes excessively large, the chromatic aberration of magnification cannot be corrected adequately. In a case of exceeding an upper limit value of conditional expression (4), Abbe number for the third lens becomes excessively large. In this case, when an attempt is made to select an optical glass to be used for the third lens from existing optical glasses, an optical glass that can be selected, automatically, becomes an optical glass having a small refractive index. Consequently, it is not possible to correct adequately aberrations such as the coma and the astigmatism.

By satisfying conditional expressions (1), (2), (3), and (4) simultaneously, it is possible to realize an objective optical system for endoscope which can deal with the small-sizing of the optical system and the large number of pixels of the image pickup element, which is strong with respect to a variation in performance within a range of the manufacturing error, and in which the peripheral resolution is not susceptible to be degraded.

Moreover, in the objective optical system for endoscope of the present embodiment, it is preferable that the following conditional expression (5) be satisfied:

$$0.8 \leq IH/f \leq 1 \tag{5}$$

where,

IH denotes the maximum image height, and f denotes the focal length of the objective optical system for endoscope.

Conditional expression (5) is a conditional expression related to a widening of an angle of view of the optical system.

In a case of falling below a lower limit value of conditional expression (5), the angle of view becomes excessively small. Consequently, in an application of endoscope, the observability is degraded. Or, since the overall length of the optical system becomes long, the small-sizing of the optical system cannot be realized.

In a case of exceeding an upper limit value of conditional expression (5), the angle of view becomes excessively large. Consequently, a degradation of an imaging performance in a peripheral portion of an image becomes excessively large. Or, since the overall length of the optical system becomes excessively short, it becomes difficult to secure an adequate back focus. As a result, an assemblability of the optical system is degraded.

Moreover, in the objective optical system for endoscope of the present embodiment, it is preferable that the following conditional expression (6) be satisfied:

$$1.8 \leq BF/f \leq 2.4 \tag{6}$$

where,

BF denotes a back focus, and f denotes the focal length of the objective optical system for endoscope.

As described above, in the objective optical system for endoscope of the present embodiment, the optical system of retro-focus type has been used. Therefore, the back focus tends to be excessively long. For this reason, it is preferable to satisfy conditional expression (6). Accordingly, it is possible to secure the back focus of an appropriate length.

In a case of falling below a lower limit value of conditional expression (6), the back focus becomes excessively short. In this case, since it becomes difficult to secure a distance necessary for the focus adjustment, the assemblability of the optical system is degraded. In a case of exceeding an upper limit value of conditional expression (6), since the back focus becomes excessively long, the small-sizing of the optical system becomes difficult.

Moreover, in the objective optical system for endoscope of the present embodiment, it is preferable that the following conditional expression (7) be satisfied:

$$-2.6 \leq r2o/rcc \leq -2 \tag{7}$$

where, r2o denotes a radius of curvature of an object-side surface of the second lens, and rcc denotes a radius of curvature of a cemented surface of the cemented lens.

For realizing an optical system having a superior imaging performance, it is necessary to correct further the coma and the chromatic aberration of magnification in a balanced manner as well as to make it an optical system strong with respect to the manufacturing error. For this, it is preferable to satisfy conditional expression (7).

Conditional expression (7) is an expression in which a ratio of the radius of curvature of the object-side surface of the second lens and the radius of curvature of the cemented surface of the cemented lens is taken.

In a case of falling below a lower limit value of conditional expression (7), the radius of curvature of the object-side surface of the second lens becomes excessively large with respect to the radius of curvature of the cemented surface of the cemented lens. In this case, since the coma is not corrected adequately, the degradation of the peripheral resolution due to the manufacturing error increases. Or, since the radius of curvature of the cemented surface of the cemented lens becomes excessively small, the lens workability is degraded.

In a case of exceeding an upper limit value of conditional expression (7), the radius of curvature of the object-side surface of the second lens becomes excessively small with respect to the radius of curvature of the cemented surface of the cemented lens. In this case, the correction of the chromatic aberration of magnification becomes excessive. Or, the radius of curvature of the cemented surface of the cemented lens becomes excessively large with respect to the radius of curvature of the object-side surface of the second lens. In this case, the correction of the chromatic aberration of magnification becomes inadequate.

Here, it is preferable that the following conditional expression (7') be satisfied instead of conditional expression (7).

$$-2.6 \leq r2o/rcc \leq -2.2 \tag{7'}$$

Moreover, in the objective optical system for endoscope of the present embodiment, it is preferable that the following conditional expression (8) be satisfied:

$$-1.0 \leq (r2o \times r2i)/(rcc \times rci) \leq -0.7 \tag{8}$$

where, r2o denotes the radius of curvature of an object-side surface of the second lens, r2i denotes a radius of curvature of an image-side surface of the second lens, rcc denotes the radius of curvature of a cemented surface of the cemented lens, and rci denotes a radius of curvature of an image-side surface of the cemented lens.

By correcting favorably not only the coma and the chromatic aberration of magnification but also the curvature of field, it is possible to improve the imaging performance of the optical system. For this, it is preferable to satisfy conditional expression (8). Conditional expression (8) is an expression in which a ratio of a product of the radii of curvature of the two surfaces of the second lens and a product of the radii of curvature of the two surface of the fourth lens is taken.

In a case of falling below a lower limit value of conditional expression (8), since an absolute value of the radius of curvature of the fourth lens becomes relatively small, either the correction of the curvature of field becomes excessive or the processing of the lens becomes difficult. Moreover, since an absolute value of the radius of curvature of the second lens becomes large, the overall length of the optical system becomes long. Consequently, the small-sizing of the optical system becomes difficult.

In a case of exceeding an upper limit value of conditional expression (8), since the absolute value of the radius of curvature of the fourth lens becomes relatively large, the correction of the curvature of field becomes inadequate. Moreover, since the absolute value of the radius of curvature of the second lens becomes small, the processing of lens becomes difficult.

When conditional expressions (6), (7), and (8) are satisfied simultaneously, the optical system can be made to be further small-sized, and furthermore, it is possible to realize an objective optical system for endoscope having a superior imaging performance.

Moreover, in the objective optical system for endoscope of the present embodiment, it is preferable that the following conditional expression (9) be satisfied:

$$-1.2 \leq r2i/f2 \leq -0.9 \tag{9}$$

where, r2i denotes the radius of curvature of an image-side surface of the second lens, and f2 denotes the focal length of the second lens.

By correcting favorably not only the chromatic aberration of magnification and the curvature of field but also the spherical aberration further, it is possible to improve the imaging performance of the optical system. For this, it is preferable to satisfy conditional expression (9).

In a case of falling below a lower limit value of conditional expression (9), the focal length of the second lens becomes excessively small, and the radii of curvature of both surfaces of the second lens become small. Consequently, apart from an amount of the spherical aberration that occurs becoming large, an amount of the coma that occurs and an amount of the astigmatism that occurs also becomes large. Or, as a value of the radius of curvature of the image-side surface of the second lens becomes large, the overall length of the optical system becomes long.

In a case of exceeding an upper limit value of conditional expression (9), a value of the focal length of the second lens becomes large. As a result, the overall length of the optical system becomes long. Or, as the value of the radius of curvature of the image-side surface of the second lens becomes small, since an amount of the spherical aberration that occurs becomes excessively large, the imaging performance is degraded.

Moreover, in the objective optical system for endoscope of the present embodiment, it is preferable that the following conditional expression (10) be satisfied:

$$2 \leq r2o/f2 \leq 2.6 \quad (10)$$

where, r2o denotes the radius of curvature of an object side surface of the second lens, and f2 denotes the focal length of the second lens.

By satisfying conditional expression (10), it is possible to realize an optical system in which the imaging performance at a center and an imaging performance at a periphery are balanced further.

In a case of falling below a lower limit value of conditional expression (10), the focal length of the second lens becomes large. In this case, the overall length becomes long. Or, the radius of curvature of the object-side surface of the second lens becomes small. In this case, the refractive power of the second lens becomes excessively large. Consequently, the correction of the curvature of field becomes excessive.

In a case of exceeding an upper limit value of conditional expression (10), the radius of curvature of the object-side surface of the second lens becomes large. In this case, the correction of astigmatism becomes inadequate. Or, the focal length of the second lens becomes small. In this case, apart from an amount of the spherical aberration that occurs becoming large, an amount of the coma that occurs and an amount of the astigmatism that occurs become large. Consequently, the aberrations cannot be corrected favorably in whole.

Here, it is preferable that the following conditional expression (10') be satisfied instead of conditional expression (10).

$$2 \leq r2o/f2 \leq 2.5 \quad (10')$$

Moreover, in the objective optical system for endoscope of the present embodiment, it is preferable that the following conditional expression (11) be satisfied:

$$-1.45 \leq fc/f4 \leq -0.80 \quad (11)$$

where, fc denotes a focal length of the cemented lens, and f4 denotes the focal length of the fourth lens.

Conditional expression (11) is an expression in which a ratio of the focal length of the cemented lens and the focal length of the fourth lens is taken. For correcting the curvature of field, it is necessary that the focal length of the fourth lens has a negative value. By satisfying conditional expression (11), it is possible to correct favorably the chromatic aberration of magnification. As a result, it is possible to prevent the degradation of the peripheral resolution.

In a case of falling below a lower limit value of conditional expression (11), the focal length of the cemented lens becomes large. In this case, the overall length of the optical system becomes long. Consequently, from a view point of small-sizing of the optical system, it is not preferable to fall below the lower limit value of conditional expression (11). In a case of exceeding an upper limit value of conditional expression (11), the chromatic aberration of magnification becomes large. Therefore, it is not preferable to exceed the upper limit value of conditional expression (11).

By satisfying conditional expressions (9), (10), and (11) simultaneously, it is possible to improve further the resolution at the periphery of image.

Examples of the present invention will be described below. In aberration diagrams, a horizontal axis indicates an aberration amount. For the spherical aberration, the astigmatism, the coma, and the chromatic aberration of magnification, the unit of an amount of aberration is mm. Moreover, the unit of an amount of distortion is %. Furthermore, FIY denotes an image height and the unit thereof is mm, and FNO denotes an F-number. The unit of wavelength for an aberration curve is nm.

Example 1

Figure 2A:
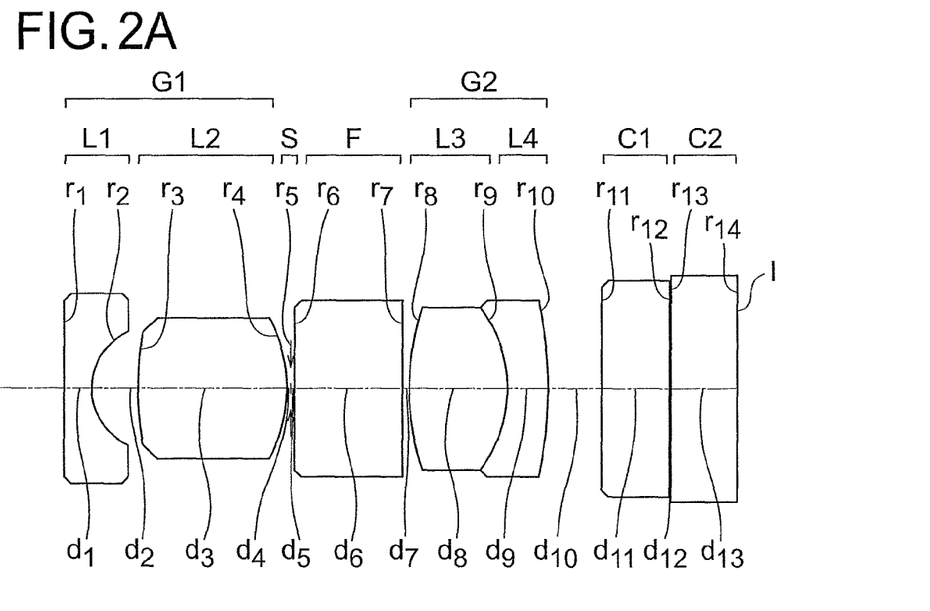
FIG. 2A is a cross-sectional view showing an arrangement of an objective optical system for endoscope according to an example 1.
Figures 2B, 2C:
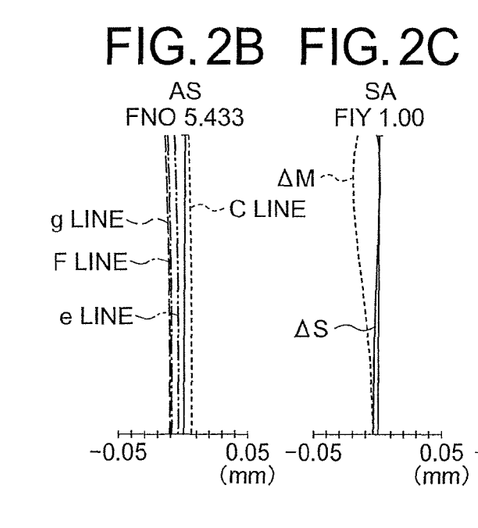
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively of the example 1.
Figure 2D:
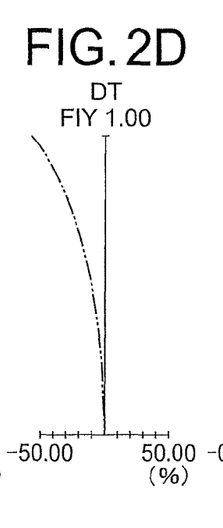
Figure 2E:
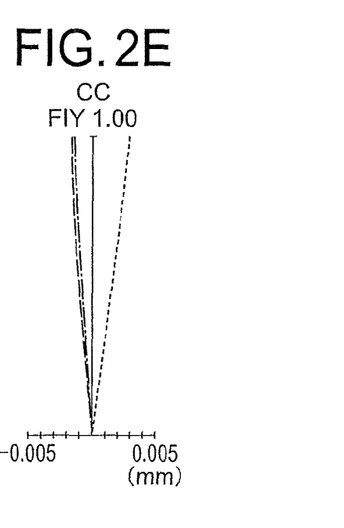

An objective optical system for endoscope according to an example 1 will be described below. FIG. 2A is a cross-sectional view showing an arrangement of the objective optical system for endoscope according to the example 1, FIG. 2B shows a spherical aberration (SA), FIG. 2C shows an astigmatism (AS), FIG. 2D shows a distortion (DT), and FIG. 2E shows a chromatic aberration of magnification (CC) of the example 1.

The objective optical system for endoscope of the example 1, as shown in FIG. 2A, includes in order from an object side, a first group G1 having a positive refractive power, an aperture stop S, and a second group G2 having a positive refractive power.

The first group G1 includes a planoconcave negative lens L1 having a flat surface directed toward the object side, and a biconvex positive lens L2.

The second group G2 includes a biconvex positive lens L3 and a negative meniscus lens L4 having a convex surface directed toward an image side. Here, the biconvex positive lens L3 and the negative meniscus lens L4 are cemented.

An optical filter F is disposed between the first group G1 and the second group G2. The optical filter F is an infra-red absorbing filter. A coating which cuts laser light of a semiconductor laser is applied to an image-side surface of the optical filter F.

Moreover, a cover glass C1 and a cover glass C2 are disposed on the image side of the second group G2. The cover glass C2 is a cover glass of a CCD. The cover glass C1 and the cover glass C2 are cemented.

Example 2

Figure 3A:
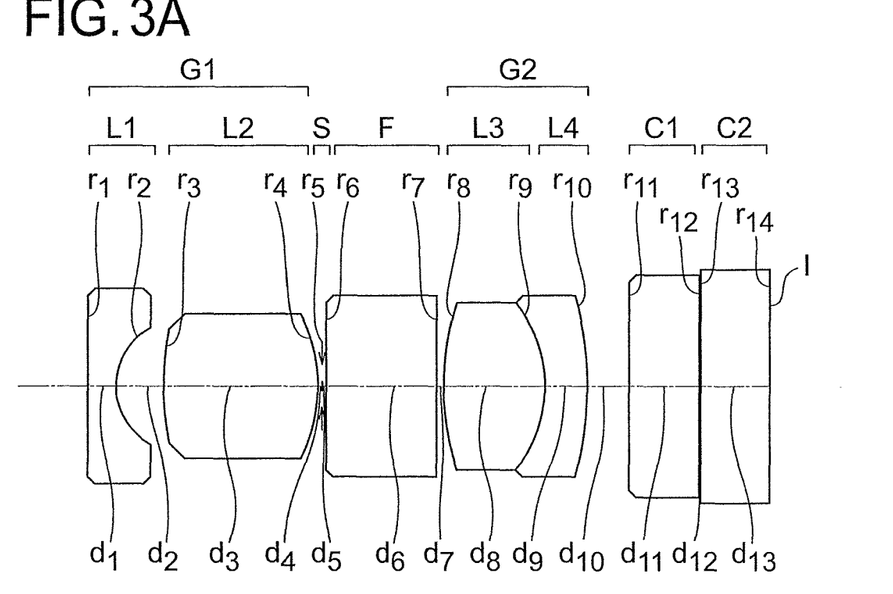
FIG. 3A is a cross-sectional view showing an arrangement of an objective optical system for endoscope according town example 2.
Figure 3B:
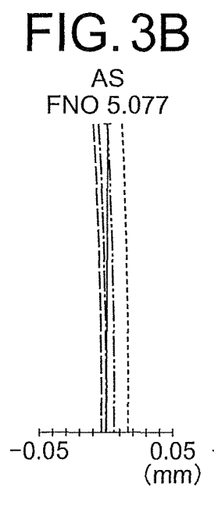
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively of the example 2.
Figure 3C:
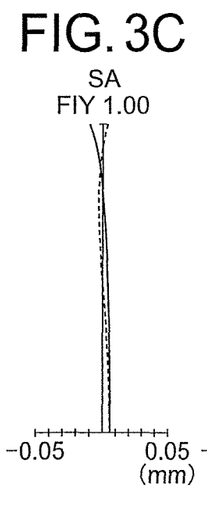
Figure 3D:
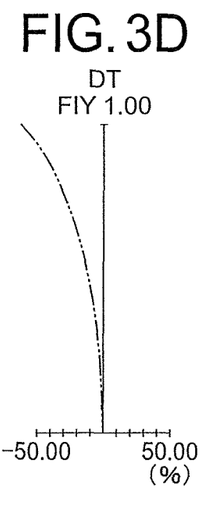
Figure 3E:
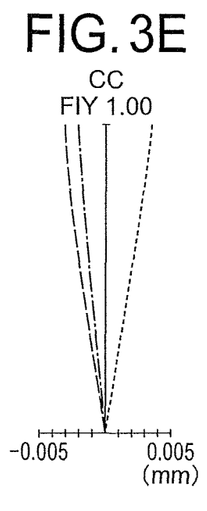

An objective optical system for endoscope according to an example 2 will be described below. FIG. 3A is a cross-sectional view showing an arrangement of the objective optical system for endoscope according to the example 2, FIG. 3B shows a spherical aberration (SA), FIG. 3C shows an astigmatism (AS), FIG. 3D shows a distortion (DT), and FIG. 3E shows a chromatic aberration of magnification (CC) of the example 2.

The objective optical system for endoscope of the example 2, as shown in FIG. 3A, includes in order from an object side, a first group G1 having a positive refractive power, an aperture stop S, and a second group G2 having a positive refractive power.

The first group G1 includes a planoconcave negative lens L1 having a flat surface directed toward the object side, and a biconvex positive lens L2.

The second group G2 includes a biconvex positive lens L3, and a negative meniscus lens L4 having a convex surface directed toward an image side. Here, the biconvex positive lens L3 and the negative meniscus lens L4 are cemented.

An optical filter F is disposed between the first group G1 and the second group G2. The optical filter F is an infra-red absorbing filter. A coating which cuts laser light of a semiconductor laser is applied to an image-side surface of the optical filter F.

Moreover, a cover glass C1 and a cover glass C2 are disposed on the image side of the second group G2. The cover glass C2 is a cover glass of a CCD. The cover glass C1 and the cover glass C2 are cemented.

Example 3

Figure 4A:
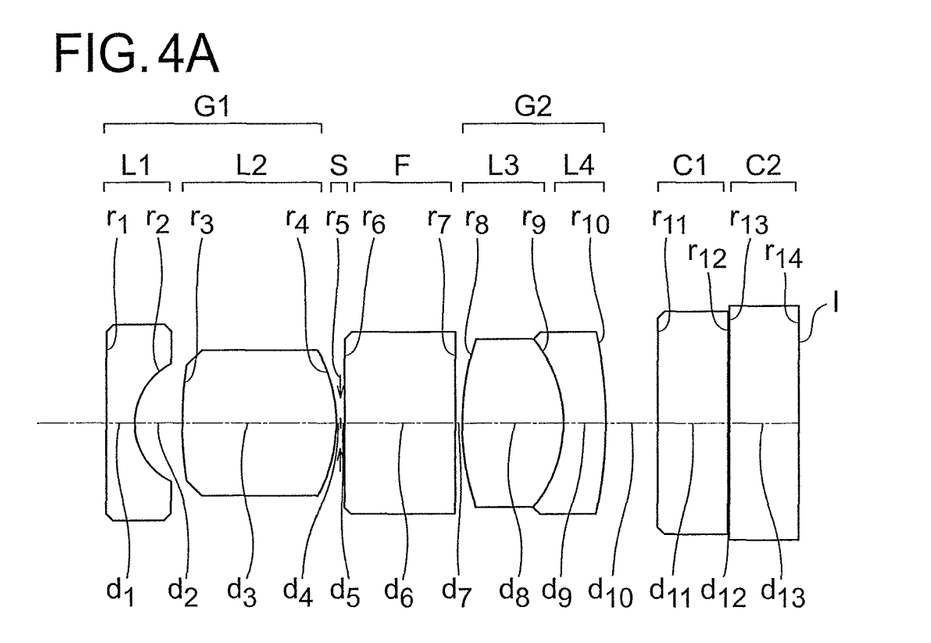
FIG. 4A is a cross-sectional view showing an arrangement of an objective optical system for endoscope according to an example 3.
Figure 4B:
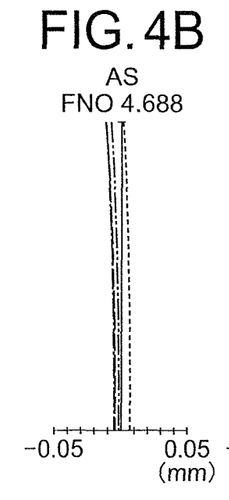
FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively of the example 3.
Figure 4C:
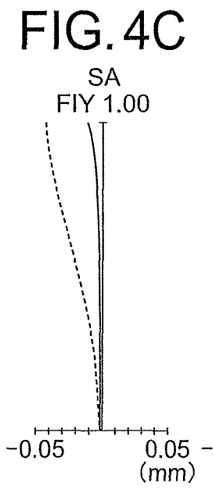
Figure 4D:
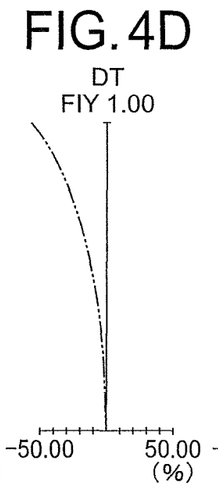
Figure 4E:
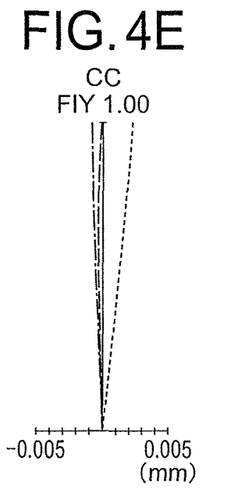

An objective optical system for endoscope according to an example 3 will be described below. FIG. 4A is a cross-sectional view showing an arrangement of the objective optical system for endoscope according to the example 3, FIG. 4B shows a spherical aberration (SA), FIG. 4C shows an astigmatism (AS), FIG. 4D shows a distortion (DT), and FIG. 4E shows a chromatic aberration of magnification (CC) of the example 3.

The objective optical system for endoscope of the example 3, as shown in FIG. 4A, includes in order from an object side, a first group G1 having a positive refractive power, an aperture stop S, and a second group G2 having a positive refractive power.

The first group G1 includes a planoconcave negative lens L1 having a flat surface directed toward the object side, and a biconvex positive lens L2.

The second group G2 includes a biconvex positive lens L3, and a negative meniscus lens L4 having a convex surface directed toward an image side. Here, the biconvex positive lens L3 and the negative meniscus lens L4 are cemented.

An optical filter F is disposed between the first group G1 and the second group G2. The optical filter F is an infra-red absorbing filter. A coating which cuts laser light of a semiconductor laser is applied to an image-side surface of the optical filter F.

Moreover, a cover glass C1 and a cover glass C2 are disposed on an image side of the second group G2. The cover glass C2 is a cover glass of a CCD. The cover glass C1 and the cover glass C2 are cemented.

Example 4

Figure 5A:
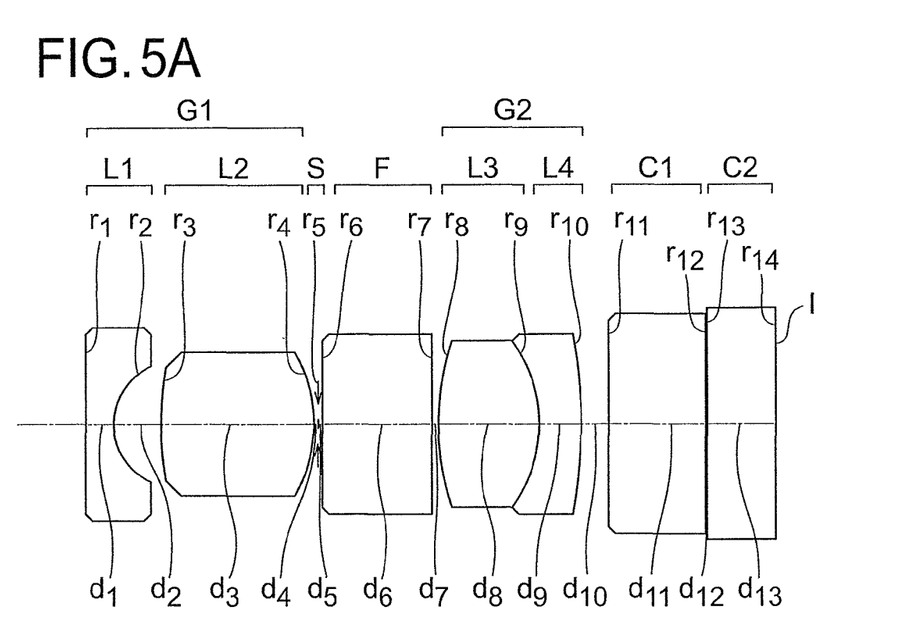
FIG. 5A is a cross-sectional view showing an arrangement of an objective optical system for endoscope according to an example 4.
Figure 5B:
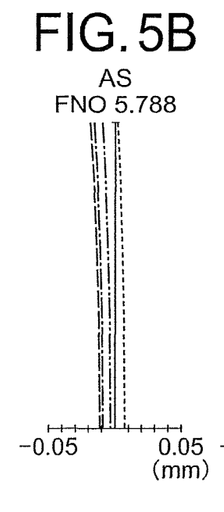
FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively of the example 4.
Figure 5C:
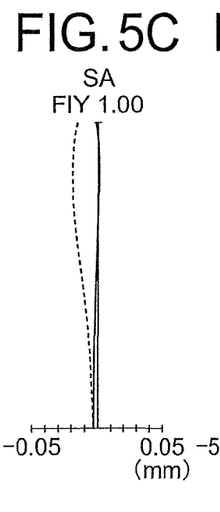
Figures 5D, 5E:
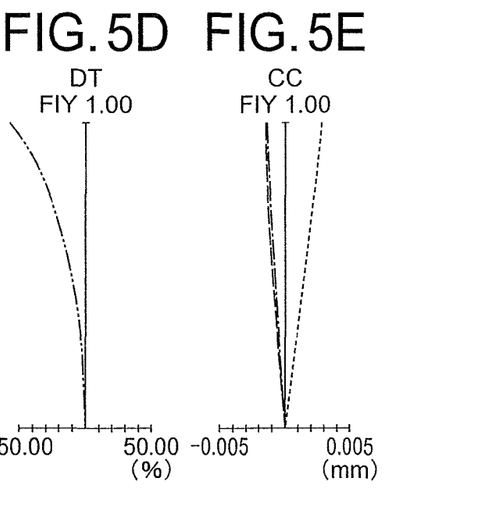

An objective optical system for endoscope according to an example 4 will be described below. FIG. 5A is a cross-sectional view showing an arrangement of the objective optical system for endoscope according to the example 4, FIG. 5B shows a spherical aberration (SA), FIG. 5C shows an astigmatism (AS), FIG. 5D shows a distortion (DT), and FIG. 5E shows a chromatic aberration of magnification (CC) of the example 4.

The objective optical system for endoscope of the example 4, as shown in FIG. 5A, includes in order from an object side, a first group G1 having a positive refractive power, an aperture stop S, and a second group G2 having a positive refractive power.

The first group G1 includes a planoconcave negative lens L1 having a flat surface directed toward the object side, and a biconvex positive lens L2.

The second group G2 includes a biconvex positive lens L3, and a negative meniscus lens L4 having a convex surface directed toward an image side. Here, the biconvex positive lens L3 and the negative meniscus lens L4 are cemented.

An optical filter F is disposed between the first group G1 and the second group G2. The optical filter F is an infra-red absorbing filter. A coating which cuts laser light of a semiconductor laser is applied to an image-side surface of the optical filter F.

Moreover, a cover glass C1 and a cover glass C2 are disposed on an image side of the second group G2. The cover glass C2 is a cover glass of a CCD. The cover glass C1 and the cover glass C2 are cemented.

Numerical data of each example described above is shown below. In symbols, r denotes radius of curvature of each surface, d denotes a thickness of each optical member or air distance, ne denotes a refractive index of each optical member for e-line, vd denotes an Abbe number for each optical member, FL denotes a focal length of the overall objective optical system for endoscope, FNO denotes an F-number, ω denotes a half angle of view, IH denotes a maximum image height. Unit of the focal length and the maximum image height is mm, and Unit of the half angle of view is ° (degree).

Example 1

Unit mm

Surface data

| Surface no. | r | d | ne | vd |
|---|---|---|---|---|
| 1 | ∞ | 0.3072 | 1.88815 | 40.76 |
| 2 | 0.7097 | 0.5222 | | |
| 3 | 3.8402 | 1.6897 | 1.83945 | 42.73 |
| 4 | −1.7020 | 0.0461 | | |
| 5(Stop) | ∞ | 0.0461 | | |
| 6 | ∞ | 1.2289 | 1.52300 | 65.13 |
| 7 | ∞ | 0.0768 | | |
| 8 | 2.9754 | 1.1060 | 1.75844 | 52.32 |
| 9 | −1.5499 | 0.4608 | 1.97189 | 17.47 |
| 10 | −4.7174 | 0.6006 | | |
| 11 | ∞ | 0.7680 | 1.51825 | 64.14 |
| 12 | ∞ | 0.0154 | 1.51500 | 64.00 |
| 13 | ∞ | 0.7680 | 1.61350 | 50.49 |
| 14(Image plane) | ∞ | | | |

Various data

| FL | 1.04766 |
|---|---|
| FNO. | 5.530 |
| ω | 66.1 |
| IH | 1 |

Example 2

Unit mm

Surface data

| Surface no. | r | d | ne | vd |
|---|---|---|---|---|
| 1 | ∞ | 0.3072 | 1.88815 | 40.76 |
| 2 | 0.7379 | 0.5222 | | |
| 3 | 3.2645 | 1.6897 | 1.83945 | 42.73 |
| 4 | −1.7569 | 0.0461 | | |
| 5(Stop) | ∞ | 0.0461 | | |
| 6 | ∞ | 1.2289 | 1.52300 | 65.13 |
| 7 | ∞ | 0.0768 | | |
| 8 | 3.0274 | 1.1060 | 1.75844 | 52.32 |
| 9 | −1.4905 | 0.4608 | 1.97189 | 17.47 |
| 10 | −3.8354 | 0.4565 | | |
| 11 | ∞ | 0.7680 | 1.51825 | 64.14 |
| 12 | ∞ | 0.0154 | 1.51500 | 64.00 |

-continued

| Unit mm | | | | |
|---|---|---|---|---|
| 13 | ∞ | 0.7680 | 1.61350 | 50.49 |
| 14(Image plane) | ∞ | | | |

| Various data | |
|---|---|
| FL | 1.03029 |
| FNO. | 5.161 |
| ω | 68.9 |
| IH | 1 |

Example 3

| Unit mm | | | | |
|---|---|---|---|---|
| Surface data | | | | |
| Surface no. | r | d | ne | vd |
| 1 | ∞ | 0.3072 | 1.88815 | 40.76 |
| 2 | 0.7179 | 0.5222 | | |
| 3 | 4.1175 | 1.6897 | 1.83945 | 42.73 |
| 4 | −1.6679 | 0.0461 | | |
| 5(Stop) | ∞ | 0.0461 | | |
| 6 | ∞ | 1.2289 | 1.52300 | 65.13 |
| 7 | ∞ | 0.0768 | | |
| 8 | 2.9343 | 1.1060 | 1.75844 | 52.32 |
| 9 | −1.4597 | 0.4608 | 1.97189 | 17.47 |
| 10 | −4.7856 | 0.5709 | | |
| 11 | ∞ | 0.7680 | 1.51825 | 64.14 |
| 12 | ∞ | 0.0154 | 1.51500 | 64.00 |
| 13 | ∞ | 0.7680 | 1.61350 | 50.49 |
| 14(Image plane) | ∞ | | | |

| Various data | |
|---|---|
| FL | 1.04767 |
| FNO. | 4.774 |
| ω | 65.7 |
| IH | 1 |

Example 4

| Unit mm | | | | |
|---|---|---|---|---|
| Surface data | | | | |
| Surface no. | r | d | ne | vd |
| 1 | ∞ | 0.3072 | 1.88815 | 40.76 |
| 2 | 0.7110 | 0.5222 | | |
| 3 | 3.8392 | 1.6897 | 1.83945 | 42.73 |
| 4 | −1.6442 | 0.0461 | | |
| 5(Stop) | ∞ | 0.0461 | | |
| 6 | ∞ | 1.2289 | 1.52300 | 65.13 |
| 7 | ∞ | 0.0768 | | |
| 8 | 2.9076 | 1.1060 | 1.75844 | 52.32 |
| 9 | −1.5669 | 0.4608 | 1.97189 | 17.47 |
| 10 | −5.4770 | 0.3072 | | |
| 11 | ∞ | 1.0753 | 1.51825 | 64.14 |
| 12 | ∞ | 0.0150 | 1.51500 | 64.00 |
| 13 | ∞ | 0.7680 | 1.61350 | 50.49 |
| 14(Image plane) | ∞ | | | |

| Various data | |
|---|---|
| FL | 1.04766 |
| FNO. | 5.899 |

-continued

| Unit mm | |
|---|---|
| ω | 65.9 |
| IH | 1 |

Next, the values of conditional expressions (1) to (11) in each example are shown below.

| Conditional expression | Example1 | Example2 |
|---|---|---|
| (1)La/Lb | 0.169 | 0.153 |
| (2)f4/f | −2.44 | −2.69 |
| (3)(ne2 × f2)/(ne4 × f4) | −0.595 | −0.539 |
| (4)vd3/vd4 | 2.99 | 2.99 |
| (5)IH/f | 0.955 | 0.97 |
| (6)BF/f | 2.05 | 1.94 |
| (7)r2o/rcc | −2.48 | −2.19 |
| (8)(r2o × r2i)/(rcc × rci) | −0.894 | −1 |
| (9)r2i/f2 | −1.04 | −1.09 |
| (10)r2o/f2 | 2.35 | 2.03 |
| (11)fc/f4 | −1.27 | −1.073 |

| Conditional expression | Example3 | Example4 |
|---|---|---|
| (1)La/Lb | 0.166 | 0.13 |
| (2)f4/f | −2.21 | −2.28 |
| (3)(ne2 × f2)/(ne4 × f4) | −0.656 | −0.62 |
| (4)vd3/vd4 | 2.99 | 2.99 |
| (5)IH/f | 0.954 | 0.954 |
| (6)BF/f | 2.02 | 2.06 |
| (7)r2o/rcc | −2.82 | −2.45 |
| (8)(r2o × r2i)/(rcc × rci) | −0.983 | −0.735 |
| (9)r2i/f2 | −1.022 | −1.03 |
| (10)r2o/f2 | 2.523 | 2.4 |
| (11)fc/f4 | −1.43 | −1.44 |

According to the present invention, it is possible to provide an objective optical system for endoscope which can deal with the small-sizing of an optical system and the large number of pixels of an image pickup element, which is strong with respect to a variation in performance within a range of a manufacturing error, and in which a peripheral resolution is not susceptible to be degraded.

As described above, the present invention is useful for the objective optical system for endoscope which can deal with the small-sizing of the optical system and the large number of pixels of an image pickup element, which is strong with respect to a variation in performance within a range of a manufacturing error, and in which a peripheral resolution is not susceptible to be degraded.

What is claimed is:
1. An objective optical system for an endoscope, the objective optical system comprising in order from an object side:
   a first group having a positive refractive power;
   an aperture stop; and
   a second group having a positive refractive power, wherein:
   the first group includes a first lens having a negative refractive power, of which an object side is a flat surface, and a second lens having a positive refractive power,
   the second group includes a cemented lens,
   the cemented lens includes a third lens having a positive refractive power and a fourth lens having a negative refractive power, and the following conditional expressions (1), (2), (3), (4), (7), and (9) are satisfied:

$$0.13 \leq La/Lb \leq 0.17 \quad (1),$$

$$-2.7 \leq f4/f \leq -2.2 \quad (2),$$

$$-0.7 \leq (ne2 \times f2)/(ne4 \times f4) \leq 0 \quad (3),$$

$$2.5 \leq vd3/vd4 \leq 3.5 \quad (4),$$

$$-2.6 \leq r2o/rcc \leq -2 \quad (7), \text{ and}$$

$$-1.2 \leq r2i/f2 \leq -0.9 \quad (9),$$

where:
La denotes a sum of air spaces along an optical axis of the objective optical system between a lens surface nearest to an object and an image plane,
Lb denotes an overall length of the objective optical system, which is a length obtained by adding a back focus to a distance from the lens surface nearest to the object to a lens surface nearest to an image, the back focus being a length from the lens surface nearest to the image to the image plane, and the back focus not being subjected to air conversion,
f4 denotes a focal length of the fourth lens,
f denotes a focal length of the objective optical system,
f2 denotes a focal length of the second lens,
ne2 denotes a refractive index for an e-line of the second lens,
ne4 denotes a refractive index for an e-line of the fourth lens,
vd3 denotes an Abbe number with reference to a d-line for the third lens,
vd4 denotes an Abbe number with reference to a d-line for the fourth lens,
r2o denotes a radius of curvature of an object-side surface of the second lens,
rcc denotes a radius of curvature of a cemented surface of the cemented lens, and
r2i denotes a radius of curvature of an image-side surface of the second lens.

2. The objective optical system according to claim 1, wherein the following conditional expression (5) is satisfied:

$$0.8 \leq IH/f \leq 1 \quad (5),$$

where IH denotes a maximum image height.

3. The objective optical system according to claim 1, wherein the following conditional expression (6) is satisfied:

$$1.8 \leq BF/f \leq 2.4 \quad (6),$$

where BF denotes the back focus.

4. The objective optical system according to claim 1, wherein the following conditional expression (8) is satisfied:

$$-1.0 \leq (r2o \times r2i)/(rcc \times rci) \leq -0.7 \quad (8),$$

where rci denotes a radius of curvature of an image-side surface of the cemented lens.

5. The objective optical system according to claim 1, wherein the following conditional expression (10) is satisfied:

$$2 \leq r2o/f2 \leq 2.6 \quad (10).$$

6. The objective optical system according to claim 1, wherein the following conditional expression (11) is satisfied:

$$-1.45 \leq fc/f4 \leq -0.80 \quad (11),$$

where fc denotes a focal length of the cemented lens.

* * * * *

UNITED STATES PATENT AND TRADEMARK OFFICE
CERTIFICATE OF CORRECTION

| | |
|---|---|
| PATENT NO. | : 9,939,627 B2 |
| APPLICATION NO. | : 15/589344 |
| DATED | : April 10, 2018 |
| INVENTOR(S) | : Yosuke Eguchi |

It is certified that error appears in the above-identified patent and that said Letters Patent is hereby corrected as shown below:

In the Specification

Column 2, Line 56, delete "town" and insert --to an--.

Signed and Sealed this
Tenth Day of July, 2018

Andrei Iancu
*Director of the United States Patent and Trademark Office*